(12) United States Patent
Mun et al.

(10) Patent No.: US 12,029,550 B2
(45) Date of Patent: Jul. 9, 2024

(54) 3D HUMAN BODY JOINT ANGLE PREDICTION METHOD AND SYSTEM USING 2D IMAGE

(71) Applicant: KOREA INSTITUTE OF SCIENCE AND TECHNOLOGY, Seoul (KR)

(72) Inventors: Kyung-Ryoul Mun, Seoul (KR); Jinwook Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 129 days.

(21) Appl. No.: 17/978,037

(22) Filed: Oct. 31, 2022

(65) Prior Publication Data
US 2023/0248261 A1     Aug. 10, 2023

(30) Foreign Application Priority Data

Feb. 9, 2022     (KR) ........................ 10-2022-0016792

(51) Int. Cl.
*A61B 5/11* (2006.01)
*A61B 5/00* (2006.01)
(Continued)

(52) U.S. Cl.
CPC .......... *A61B 5/1071* (2013.01); *A61B 5/0077* (2013.01); *A61B 5/1079* (2013.01); *A61B 5/1121* (2013.01); *A61B 5/1127* (2013.01); *A61B 5/7267* (2013.01); *A61B 5/7275* (2013.01); *G06T 7/215* (2017.01); *G06T 7/246* (2017.01); *G06T 7/292* (2017.01); *A61B 2562/04* (2013.01);
(Continued)

(58) Field of Classification Search
CPC ... A61B 5/1071; A61B 5/0077; A61B 5/1079; A61B 5/1121; A61B 5/1127; A61B 5/7267; A61B 5/7275; A61B 2562/04; A61B 5/1128; A61B 5/1114; A61B 5/1116; A61B 5/112; A61B 5/0033; G06T 7/215; G06T 7/246; G06T 7/292; G06T 2207/20081; G06T 2207/20084; G06T 2207/30196; G06T 2207/30204; G06T 7/60; G06T 2207/10016
See application file for complete search history.

(56) References Cited

U.S. PATENT DOCUMENTS 10,842,415 B1    11/2020   Janannathan et al.
2017/0316578 A1   11/2017   Fua et al.

FOREIGN PATENT DOCUMENTS

KR    10-2016-0097044 A    8/2016
KR    10-2021-0103876 A    8/2021
WO    WO 2017/166019 A1   10/2017

OTHER PUBLICATIONS

Toshev, Alexander, and Christian Szegedy. "Deeppose: Human pose estimation via deep neural networks." *Proceedings of the IEEE conference on computer vision and pattern recognition.* 2014.
(Continued)

*Primary Examiner* — Bo Joseph Peng
(74) *Attorney, Agent, or Firm* — NSIP Law

(57) ABSTRACT

A system for predicting a three-dimensional human body joint angle according to an embodiment predicts information on a human body joint angle of a new subject by photographing a motion of a subject at different three-dimensional positions and using information on the human body joint angle according to the generated motion of the subject and information on the human body joint angle according to the motion of the subject.

13 Claims, 14 Drawing Sheets

(51) Int. Cl.
    *A61B 5/107*     (2006.01)
    *G06T 7/215*     (2017.01)
    *G06T 7/246*     (2017.01)
    *G06T 7/292*     (2017.01)

(52) U.S. Cl.
    CPC ............... *G06T 2207/20081* (2013.01); *G06T 2207/20084* (2013.01); *G06T 2207/30196* (2013.01); *G06T 2207/30204* (2013.01)

(56) References Cited

OTHER PUBLICATIONS

Newell, Alejandro, Kaiyu Yang, and Jia Deng. "Stacked hourglass networks for human pose estimation." *European conference on computer vision.* Springer, Cham, 2016.

Cao, Zhe, et al. "Realtime multi-person 2d pose estimation using part affinity fields." *Proceedings of the IEEE conference on computer vision and pattern recognition.* 2017.

Martinez, Julieta, et al. "A simple yet effective baseline for 3d human pose estimation." *Proceedings of the IEEE international conference on computer vision.* 2017.

Pavllo, Dario, et al. "3d human pose estimation in video with temporal convolutions and semi-supervised training." *Proceedings of the IEEE/CVF Conference on Computer Vision and Pattern Recognition.* 2019.

3D HUMAN BODY JOINT ANGLE PREDICTION METHOD AND SYSTEM USING 2D IMAGE

DESCRIPTION OF GOVERNMENT-SPONSORED RESEARCH

This study was made with the support of the Ministry of Science and ICT [Main Project name Development of data-based health monitoring and prediction technology for new normal healthcare, Main Project Identification Number: 2E31051] and [Sub-Project name: Development of artificial intelligence-based personalized exercise management platform and service to improve muscle function and prevent muscle loss in middle-aged people, Sub-Project Identification Number: 2N62280]

CROSS-REFERENCE TO RELATED APPLICATION

The present application claims priority to Korean Patent Application No. 10-2022-0016792, filed Feb. 9, 2022, the entire contents of which are incorporated herein for all purposes by this reference.

BACKGROUND OF THE INVENTION

Field of the Invention

It relates to a system and method for predicting a three-dimensional human body joint angle using a two-dimensional image. Particularly, it relates to a method and system for predicting a three-dimensional human body joint angle by suggesting a method for obtaining a data set capable of measuring information on a three-dimensional joint angle regardless of the position and angle of a camera, and using a two-dimensional images obtained from various angles and positions.

Description of the Related Art

The motion and gait of the human body contain various information on personal information, pathological symptoms, and motion intentions, so it is important to quantitatively analyze them. The most representative kinematic information for quantification of motion and gait is the joint angle of the segment of the human body, and it is used to diagnose and monitor patients with musculoskeletal disorders. Those who have undergone orthopedic surgery, and various geriatric diseases of the elderly, and for the performance improvement and rehabilitation of sports players.

A method for measuring a joint angle in which several expensive infrared cameras are used, a retroreflective marker is attached to the subject's body located in a fixed space to obtain the three-dimensional coordinates of the marker, and the human joint angle based on this is measured has been proposed. However, this conventional art required expensive equipments and experienced experimenters, and it was impossible to measure the joint angle anywhere due to lack of mobility.

In addition, as disclosed in Korean Patent Laid-Open Publication No. 10-2016-0097044, a device for measuring a human body joint rotation angle including an acceleration sensor and a gyro sensor has been proposed. However, although it is possible to measure a three-dimensional angle through such a conventional device, wearing a sensor is cumbersome, and there are limitations that require many post-processing processes such as sensor calibration, sensor fusion, data processing, and filtering for accurate measurement.

Also, there are studies on predicting information on a human body joint from a current image, but mainly because a two-dimensional joint angle is predicted using manually labeled data for the position information of the joint, the predicted human body joint angle is changed according to the position and angle of a camera so that there is a limitation in outputting inaccurate results.

SUMMARY OF THE INVENTION

The present invention has been devised to solve the above problems, and the present invention relates to a method and system for predicting a three-dimensional human body angle using a two-dimensional image obtained from various angles and positions regardless of a subject's clothes and environment.

A system for predicting a three-dimensional human body joint angle using a two-dimensional image according to an embodiment of the present invention includes a first training data generator including a plurality of cameras that generates a motion image of a subject by photographing a motion of the subject to which a plurality of markers is attached at different three-dimensional positions, and an optical motion analyzer that generates information on a human body joint angle according to the motion of the subject through the plurality of markers; a second training data generator including the plurality of cameras that generate the motion image of the subject by photographing the motion of the subject to which an electronic goniometer is attached at the different three-dimensional positions, and an electronic angle analyzer that generates the information on the human body joint angle according to the motion of the subject through the electronic goniometer; a training data set constructor that constructs input data by combining the motion images respectively provided from the first training data generator and the second training data generator, constructs output data by combining the information on the human body joint angle respectively provided from the first training data generator and the second training data generator, and generates a training data set by mapping the output data corresponding to the input data to the input data; a model trainer that trains a predictive model for predicting the information on the human body joint angle according to the motion image of the subject using the training data set; and a joint angle predictor that predicts the information on the human body joint angle of the subject based on the motion image of a new subject using the trained predictive model.

A method for predicting a three-dimensional human body joint angle using a two-dimensional image according to an embodiment of the present invention is performed in a system for predicting the three-dimensional human body joint angle using the two-dimensional image. The method includes the steps of constructing a predictive model; acquiring a motion image of a subject; and predicting information on a human body joint angle of the subject by using the trained predictive model. The step of constructing a predictive model includes a first step of generating the motion image of the subject by photographing a motion of the subject at different three-dimensional positions, and generating the information on the human body joint angle according to the motion of the subject through a plurality of markers attached to the subject; a second step of generating the motion image of the subject by photographing the motion of the subject at the different three-dimensional positions, and generating the information on the human body joint angle according to the motion of the subject through an electronic goniometer attached to the subject; a third step of constructing input data by combining the motion images respectively generated through the first and second steps, constructing output data by combining the information on the human body joint angle respectively generated through the first and second steps, and generating a training data set by mapping the output data corresponding to the input data to the input data; and a fourth step of training the predictive model for predicting the information on the human body joint angle according to the motion image of the subject by using the training data set.

The system and method for predicting a three-dimensional human body joint angle using a two-dimensional image according to an embodiment of the present invention can predict the information on the human body joint angle of the subject by inputting the two-dimensional images obtained at various angles and positions into the prediction model. That is, regardless of the position and angle of the camera, it is possible to provide the information on the human body joint angle of the subject only with the photographed two-dimensional image.

In addition, the predictive model according to an embodiment of the present invention is trained by constructing the output data by applying the optical marker method and the electronic goniometer method together, so that it is possible to take the two-dimensional image in a state more suitable to the actual environment of the subject without restrictions on the subject's clothes and environment, and it is possible to provide the information on the three-dimensional joint angle to the subject regardless of the subject's clothes and environment, and the position and angle of the camera.

DETAILED DESCRIPTION OF THE INVENTION

Hereinafter, preferred embodiments according to the present invention will be described in detail with reference to the accompanying drawings. The detailed description set forth below in conjunction with the appended drawings is intended to describe exemplary embodiments of the present invention and is not intended to represent the only embodiments in which the present invention may be practiced. The following detailed description includes specific details in order to provide a thorough understanding of the present invention. However, one skilled in the art will recognize that the present invention may be practiced without these specific details. Specific terms used in the following description are provided to help the understanding of the present invention, and the use of these specific terms may be changed to other forms without departing from the technical spirit of the present invention.

Figure 1:
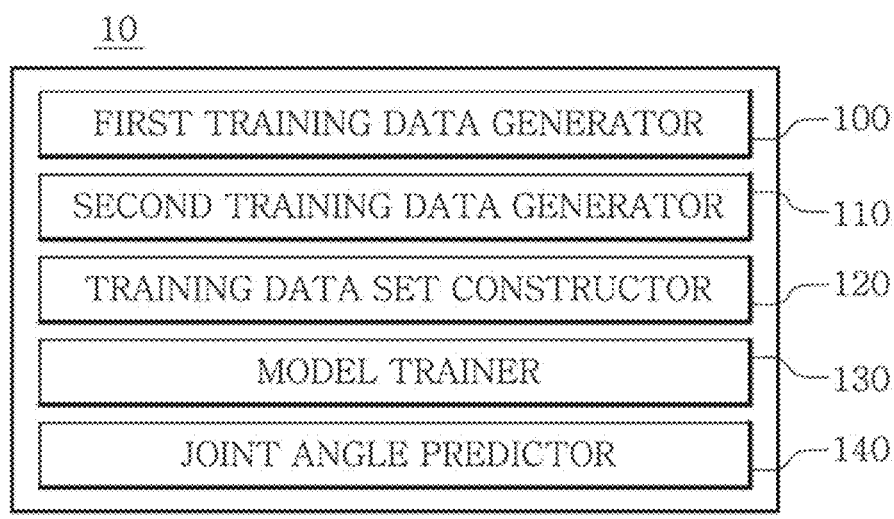
FIG. 1 is a block diagram of a system for predicting a three-dimensional human body joint angle using a two-dimensional image according to an embodiment of the present invention.
Figure 2:
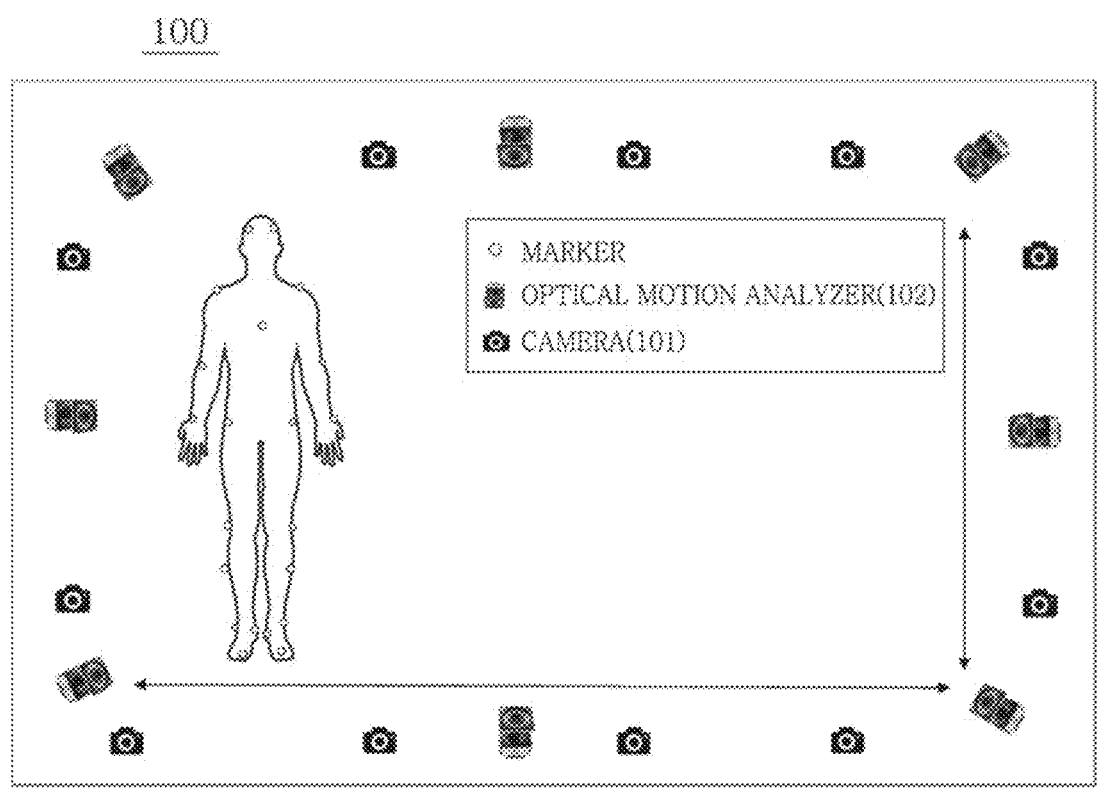
FIG. 2 shows a diagram schematically illustrating a first training data generator according to an embodiment of the present invention.
Figure 3:
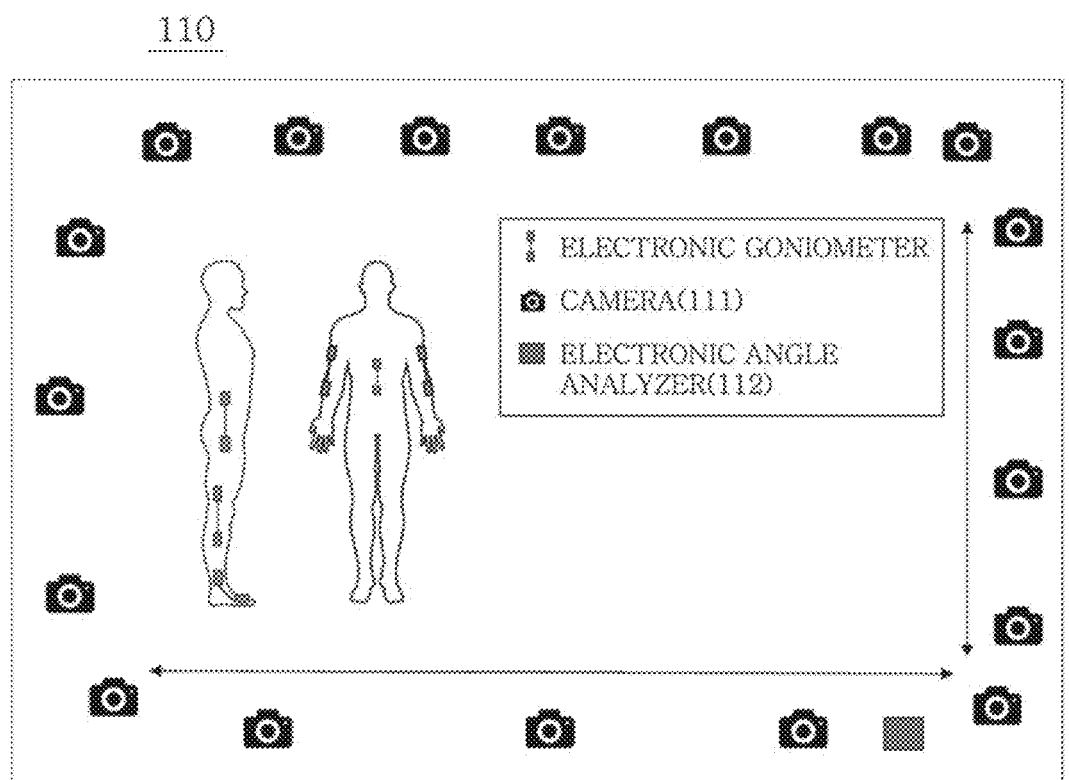
FIG. 3 shows a diagram schematically illustrating a second training data generator according to an embodiment of the present invention.
Figure 4:
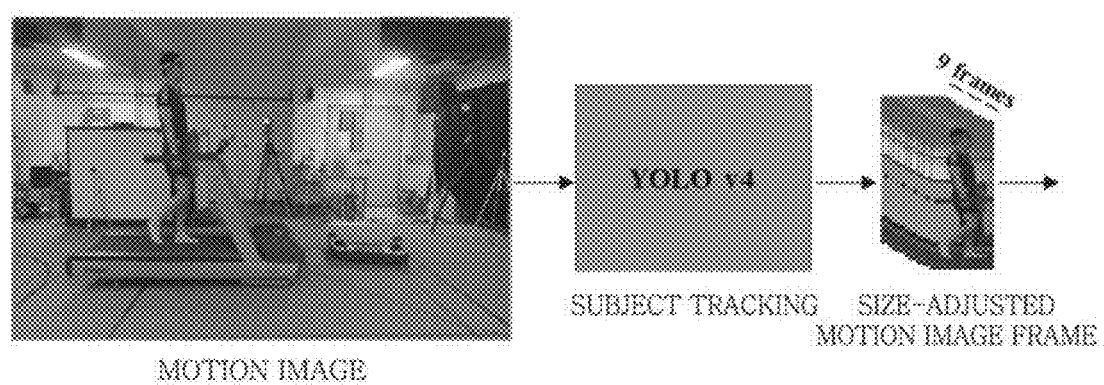
FIG. 4 is a diagram schematically illustrating a preprocessing process according to an embodiment of the present invention.
Figure 5:
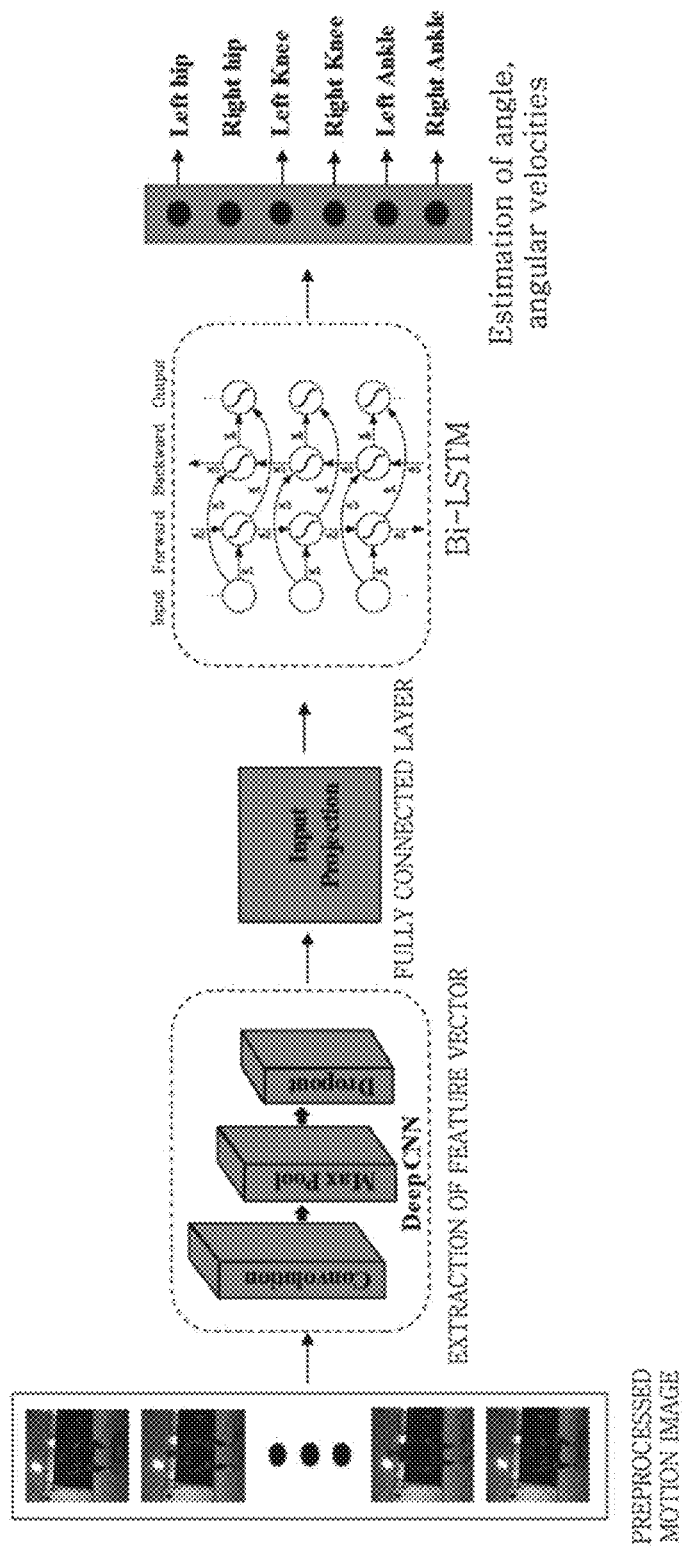
FIG. 5 shows a structure of a predictive model according to an embodiment of the present invention.

FIG. 1 is a block diagram of a system for predicting a three-dimensional human body joint angle using a two-dimensional image according to an embodiment of the present invention. FIG. 2 shows a diagram schematically illustrating a first training data generator according to an embodiment of the present invention. FIG. 3 shows a diagram schematically illustrating a second training data generator according to an embodiment of the present invention. FIG. 4 is a diagram schematically illustrating a preprocessing process according to an embodiment of the present invention. FIG. 5 shows a structure of a predictive model according to an embodiment of the present invention.

Referring to FIGS. 1 to 5, a system for predicting a three-dimensional human body joint angle using a two-dimensional image 10 includes a first training data generator 100, a second training data generator 110, and a training data set constructor 120, a model trainer 130, and a joint angle predictor 140.

The system for predicting a three-dimensional human body joint angle using a two-dimensional image according to embodiments may be entirely hardware, or may be partly hardware and partly software in one aspect. For example, the system for predicting a three-dimensional human body joint angle using a two-dimensional image of the present specification and each unit included therein may collectively refer to a device for exchanging data in a specific format and content in an electronic communication method and software related thereto. As used herein, terms such as "unit", "module", "server", "system", "device" or "terminal" are intended to refer to a combination of hardware and software driven by the hardware. For example, the hardware herein may be a data processing device including a CPU or other processor. In addition, the software-driven by the hardware may refer to a running process, an object, an executable file, a thread of execution, a program, and the like.

In addition, each part constituting the system for predicting a three-dimensional human body joint angle using a two-dimensional image is not necessarily intended to refer to a physically distinct separate component. Although the first training data generator 100, the second training data generator 110, the training data set constructor 120, the model trainer 130, and the joint angle predictor 140 are shown in FIG. 1 as separate blocks different from each other, this is merely a functional division of the devices constituting the system for predicting a three-dimensional human body joint angle using a two-dimensional image by the operations performed by the devices. Accordingly, according to an embodiment, some or all of the first training data generator 100, the second training data generator 110, the training data set constructor 120, the model trainer 130, and the joint angle predictor 140 may be integrated in the same single device, one or more may be implemented as separate devices physically separated from other parts, and may be components communicatively connected to each other in a distributed computing environment.

The first training data generator 100 and the second training data generator 110 may generate input data for constructing a predictive model and output data that is a ground truth corresponding to the input data, respectively. The input data may be motion images of the subject generated from a plurality of cameras disposed at different three-dimensional positions, and the output data may be information on a human body joint angle according to the motion of the subject. The first training data generator 100 and the second training data generator 110 may have the same method of photographing the motion image of the subject, the input data for training, but may have different methods for generating the output data, the information on the human body joint angle according to the subject's motion.

Specifically, referring to FIG. 2, the first training data generator 100 includes a plurality of cameras 101 that generates the motion image of the subject by photographing the subject's motion at different three-dimensional positions and an optical motion analyzer 102 that generates information on the human body joint angle according to the motion of the subject through a plurality of markers attached to the subject. The plurality of cameras 101 may be disposed at different three-dimensional positions to simultaneously photograph the motion of the subject. The plurality of cameras 101 may be mobile cameras that are easy to carry, but are not limited thereto. That is, the motion image of the subject may include a plurality of images taken from different angles. The plurality of cameras 101 may synchronize with a sensing time point, and may generate a two-dimensional image at the same time point.

The subject with the plurality of markers may take at least one of gait, treadmill gait, exercise motion, and daily life motion, and the plurality of cameras 101 may generate a motion image by photographing the motions of the subject. Accordingly, the generated motion image of the subject may include at least one of a gait image of the subject walking on a general flat ground, a treadmill gait image of the subject walking on a treadmill, an exercise motion image of the subject performing an exercise motion, and a daily life motion image of the subject performing the motion occurring in daily life. The gait image corresponds to the photographed image of the subject performing a motion such as normal walking, slow walking, fast walking, changing direction, and walking in place. The treadmill motion corresponds to the photographed image of the subject performing a motion such as normal walking, slow walking, fast walking, and running slowly on the treadmill. The exercise motion image corresponds to the photographed image of the subject performing a motion such as running slowly, squatting, arm stretching, jumping in place, balancing two feet, balancing one leg, and the like. The daily life motion image corresponds to the photographed image of the subject performing a motion such as climbing/descending stairs, climbing/descending an incline, sitting/standing, lying/standing, lying/sitting, and the like.

The optical motion analyzer 102 may recognize the three-dimensional position of each of the plurality of markers attached to the subject, and generate information on the human body joint angle according to the subject's motion based on the recognized three-dimensional position of the marker. The optical motion analyzer 102 may be configured to synchronize the plurality of cameras 101 and the sensing time point. The subject may perform the above-described motion in a state in which the plurality of markers is attached to the subject, and the photographed image of the subject performing the motion and the information on the human body joint angle according to the motion may be generated together. In an embodiment, the optical motion analyzer 102 may emit infrared rays to the subject and recognize the three-dimensional position of the marker by re-recognizing the infrared rays reflected by the marker mounted on the subject. However, the present invention is not limited thereto, and the marker mounted on the subject may be a self-luminous marker, and the optical motion analyzer 102 may recognize the light emitted from each marker, thereby recognizing the three-dimensional position of the marker.

As shown in FIG. 2, the plurality of markers may be attached to major joints and segments of the human body. For example, the plurality of markers may be attached to a shoulder, an elbow, a wrist, a pelvis, a knee, a calf, an ankle, a toe, and the like. The information on the human body joint angle may include a three-dimensional angle of at least one of the subject's ankle, knee, hip joint, elbow, and torso and a three-dimensional angular velocity of at least one of the subject's ankle, knee, hip joint, elbow and torso. That is, the optical motion analyzer 102 may analyze the three-dimensional position of the plurality of markers attached to major joints and segments of the subject's body, and may generate the three-dimensional angle of at least one of the subject's ankle, knee, hip joint, elbow, and torso and the three-dimensional angular velocity of at least one of the subject's ankle, knee, hip joint, elbow, and torso.

Here, the plurality of markers is attached to major joints and segments of the human body, and in order to efficiently operate with the markers, there is a limitation in the subject's clothes. In other words, since the recognition of markers may be hindered in the case of casual clothes worn by the subject in daily life, the subject has to wear special equipment such as a motion capture suit, or wear short-sleeved clothing that exposes the body to the outside, such as short sleeves and shorts. The method of generating result data using the plurality of markers may cause problems in that the accuracy and predictive ability of the constructed predictive model are deteriorated as the clothes of the subject are limited and the environment in which the experiment is performed is limited.

The second training data generator 110 may be configured to generate training data that can supplement the training data of the first training data generator 110 generated through the optical motion analyzer using such a marker. Specifically, referring to FIG. 3, the second training data generator 110 may include a plurality of cameras 111 that generates the motion image of the subject by photographing the motion of the subject with an electronic goniometer at different three-dimensional positions and an electronic angle analyzer 112 that generates information on the human body joint angle according to the motion of the subject through the electronic goniometer. The plurality of cameras 101 may be disposed at different three-dimensional positions to simultaneously photograph the motion of the subject. The plurality of cameras 111 may be mobile cameras that are easy to carry, but are not limited thereto. That is, the motion image of the subject may include a plurality of images taken from different angles. The plurality of cameras 111 may be synchronized with the sensing time point, and the plurality of cameras may generate a two-dimensional image at the same time point.

The subject with the electronic goniometer may take at least one of gait, treadmill gait, exercise motion, and daily life motion, and the plurality of cameras 111 may generate a motion image by photographing the motion of the subject. The gait, treadmill gait, exercise motion, and daily life motion in the second training data generator 110 are the same as in the first training data generator 110, and redundant descriptions will be omitted.

As shown in FIG. 2, the electronic goniometer may be attached to the human body to confirm changes in major joints and segments of the human body. The electronic goniometer may include a bending part extending between the attachment parts attached to the human body, and the bending part may be positioned to correspond to major joints and segments of the human body. For example, the electronic goniometer may be attached to the subject's lower extremity, elbow, and torso, and the bending part may be bent in response to major changes in the human body, for example, bending the arm. The electronic angle analyzer 112 may detect a change in the bending part to generate the information on the subject's body joint angle. The information on the human body joint angle may include the three-dimensional angle of at least one of the subject's ankle, knee, hip joint, elbow, and torso and the three-dimensional angular velocity of at least one of the subject's ankle, knee, hip joint, elbow and torso. That is, the electronic angle analyzer 112 may analyze changes in the plurality of electronic goniometers attached to the subject's body, and generate the three-dimensional angle of at least one of the subject's ankle, knee, hip joint, elbow and torso and the three-dimensional angular velocity of at least one of the subject's ankle, knee, hip joint, elbow, and torso.

The electronic angle analyzer 112 may be configured to synchronize the plurality of cameras 111 and the sensing time point. The subject can perform the above-described motion without being exposed to the outside by covering the electronic goniometer with clothes, and the photographed motion image of the subject performing the motion and the information on the human body joint angle according to the motion can be generated together. The electronic goniometer may be covered by the subject's clothing so as not to be exposed to the outside. The electronic goniometer is positioned inside the clothes and may be changed in response to a change in the human body, and the electronic angle analyzer 112 may receive this change degree. As the electronic goniometer is positioned inside the subject's clothes, training data in various clothes and various environments may be generated, and the training data generated by the second training data generator 110 may supplement the training data generated in the first training data generator 100.

The training data set constructor 120 may construct input data by collecting the motion images respectively provided from the first training data generator 100 and the second training data generator 110, and may construct output data by collecting the information on the human body joint angle respectively provided from the first training data generator 100 and the second training data generator 110. The training data set constructor 120 may generate a training data set by mapping the output data corresponding to the input data to the input data. The input data corresponds to the photographed two-dimensional image of the subject performing the motion at a specific angle, and the output data, which is a ground truth corresponding to this, may include the three-dimensional angle of at least one of the ankle, knee, hip joint, elbow, and torso of the subject performing the motion, and the three-dimensional angular velocity of at least one of the ankle, knee, hip joint, elbow, and torso of the subject.

Here, the training data set constructor 120 may first perform preprocessing on the provided motion image and then construct the training data set. The training data set constructor 120 may apply an algorithm for detecting a person in an original motion image. The training data set constructor 120 may apply a YOLO algorithm and track the subject in the entire original motion image to generate a bounding box. In addition, the training data set constructor 120 may extract the subject from the image based on the generated bounding box and then adjust the size of the image to a predetermined size. In addition, the training data set constructor 120 may further perform preprocessing of normalizing the image of the adjusted size using the average and standard deviation pixel value of an ImageNet data set. The training data set constructor 120 constructs the training data by mapping the corresponding output data to the input data, which is the pre-processed motion image.

The model trainer 130 may train a predictive model for predicting the information on the human body joint angle according to the motion image of the subject by using the training data set.

The predictive model may be configured to predict the three-dimensional joint angle of at least one of the subject's ankle, knee, hip joint, elbow and torso according to the subject's motion image, and the three-dimensional joint angle of at least one of the subject's ankle, knee, hip joint, elbow and torso according to the subject's motion image. In an embodiment, when there is a plurality of types of motion images of the subject, for example, a squat motion image and a treadmill motion image, a predictive model may be configured individually for each type, but is not limited thereto. The predictive model may be configured to predict the information on the human body joint angle for motion image according to the plurality of types.

The model trainer 130 may generate the predictive model through a machine learning method (deep learning) based on an artificial neural network (ANN) that imitates the information processing method of the human brain, which discovers patterns in numerous data and then distinguishes objects, and performs machine learning so that the computer can distinguish objects. That is, the model trainer 130 uses the two-dimensional image of the photographed subject performing a motion at a specific angle as the input data, and may construct an abstract model that outputs the three-dimensional angle of at least one of the ankle, knee, hip joint, elbow, and torso of the subject performing the motion, and the three-dimensional angular velocity of at least one of the ankle, knee, hip joint, elbow, and torso of the subject as the output data. The model trainer 130 may use a deep neural network model in which multiple hidden layers exist between an input layer and an output layer, and a convolutional neural network model that forms a connection pattern between neurons similar to the structure of the visual cortex of an animal. For example, the model trainer 130 may be configured by applying a conventional neural network model such as Densenet121, ResNet18, or ResNet50.

In addition, as shown in FIG. 5, a predictive model may be constructed using a network structure that further applies a bi-directional convolutional LSTM layer (Bi-LSTM) to a deep convolutional neural network (DeepCNN) model, and may be configured to predict the angle and angular velocity of right and left hip joints, right and left ankles, right and left knees. The LSTM layer is structured so that the output value output from the previous LSTM cell is received by the next LSTM cell as an input. That is, since the output value of the LSTM cell in a previous step is input to the LSTM cell in the next step, time-series features of a plurality of feature vectors can be extracted. Here, when the LSTM layer is configured as a bidirectional convolutional LSTM layer as shown in FIG. 5, LSTM cells connected along the reverse direction opposite to the forward direction described above may be further included in the LSTM layer. The plurality of feature vectors extracted from the neural network (Deep-CNN) model is sequentially input to the LSTM cell in the forward direction and the LSTM cell in the reverse direction, and the output value of the previous LSTM cell may also be input. Such a bidirectional convolutional LSTM layer may be a network more suitable for image analysis, and a more accurate predictive model may be implemented.

The joint angle predictor 140 predicts a three-dimensional joint angle of a new subject by using the generated predictive model.

For a new subject, only a two-dimensional image is acquired through the plurality of cameras 101 of the first training data generator 100 or the plurality of cameras 111 of the second training data generator 110. In addition, the new subject will generate a motion image without restrictions on clothing and environment, and prediction of the information on the subject's body joint angle may be provided only with the generated image.

The system for predicting a three-dimensional human body joint angle according to an embodiment of the present invention can predict the three-dimensional joint angle of a new subject by simply acquiring a two-dimensional image by using the constructed predictive model. Accordingly, the input of equipment and manpower required for the three-dimensional joint angle prediction can be reduced. Since it is a simple test, it is possible to easily provide the information on the actual three-dimensional joint angle to the patient with many difficulties in movement.

In addition, since a predictive model is constructed through the motion images of the subject photographed at various positions, it may be possible to analyze images photographed at various camera positions and angles and provide information on the human body joint angle corresponding thereto.

In addition, in addition to the training data generated by recognizing the plurality of markers, additional training is performed with the data generated through the electronic goniometer positioned inside the subject's clothes, thereby overcoming the restrictions that may be caused by the user's clothes and environment, and providing more accurate results to the subject.

EXAMPLES

An experiment to evaluate the performance of the system for predicting a three-dimensional human body joint angle using a two-dimensional image was performed as follows.

Eight optical cameras and six digital cameras were used, and the eight optical cameras and six digital cameras were synchronized so that the generation time points are generate, and generated the first training data. The second training data were generated by the six digital cameras of the subject and the electronic goniometer attached the subject. The subjects were twelve adults, and as motion images, treadmill walking and squat motions were performed. The digital camera was placed on the front, back, and side of the subject to generate motion images according to different angles, respectively, and the joint angle and joint angular velocity of the subject corresponding to each motion image were measured through the optical camera and the electronic goniometer, and training data were constructed. The constructed training data was subjected to the preprocessing process of tracking the subject in the motion image by applying YOLO (You Only Look Once), and extracting and resizing (448× 448) of the motion image based on this. A predictive model was constructed using at least one architecture among Densenet121, ResNet18, and ResNet50 through the preprocessed input data and the resulting data set.

Experimental Example 1

Figure 6A:
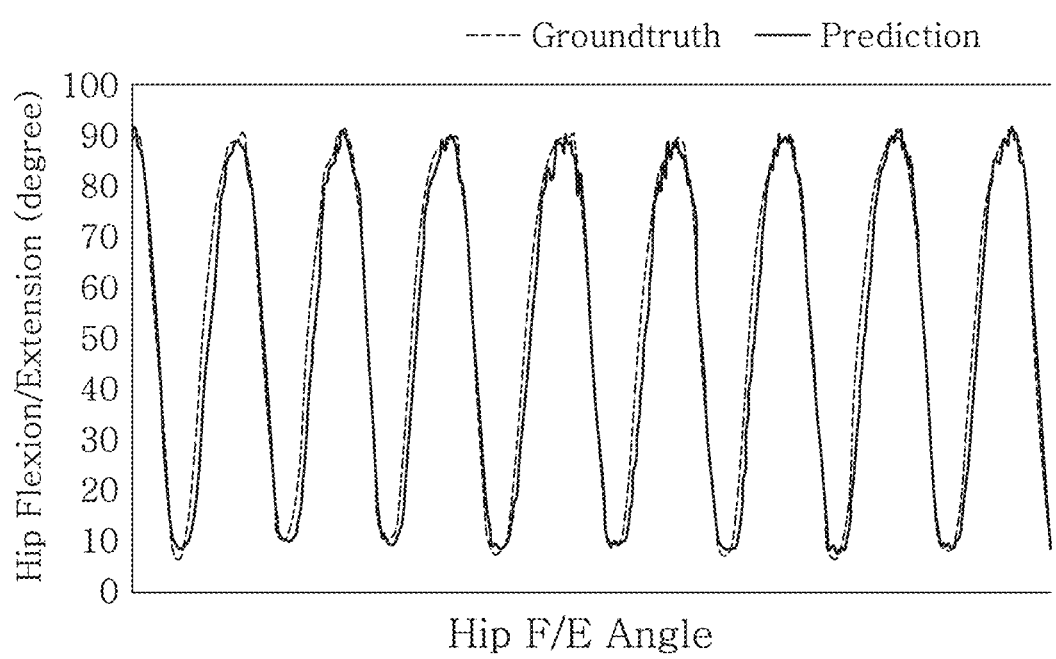
FIGS. 6A and 6B are graphs illustrating the joint angle prediction performance of a predictive model according to an embodiment of the present invention.
Figure 6B:
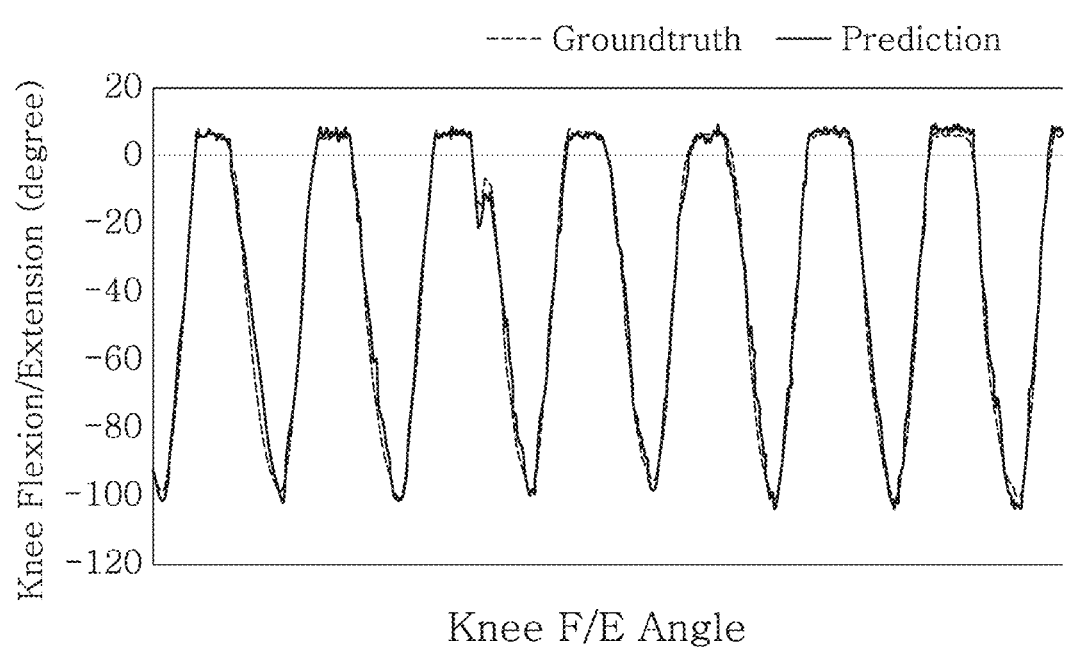

A predictive model was constructed based on Densenet121, and its joint angle prediction performance was confirmed. FIGS. 6A and 6B are graphs illustrating the joint angle prediction performance of a predictive model according to an embodiment of the present invention.

FIG. 6A is a graph comparing a prediction and a ground truth for a change in hip flexion/extension, and FIG. 6B is a graph comparing a prediction and a ground truth for a change in knee flexion/extension. Referring to FIGS. 6A and 6B, it can be seen that the prediction by the predictive model is calculated quite similarly to the ground truth.

Experimental Example 2

Each predictive model was individually constructed with Densenet121, ResNet18, and ResNet50, and the joint angular velocity prediction performance of the constructed predictive model was confirmed. $Cc_{norm}$ analysis of the angular velocity for each joint was used to check the symmetry between the target (correct value) and the predicted angular velocity pattern, and to confirm the prediction performance.

Figure 7A:
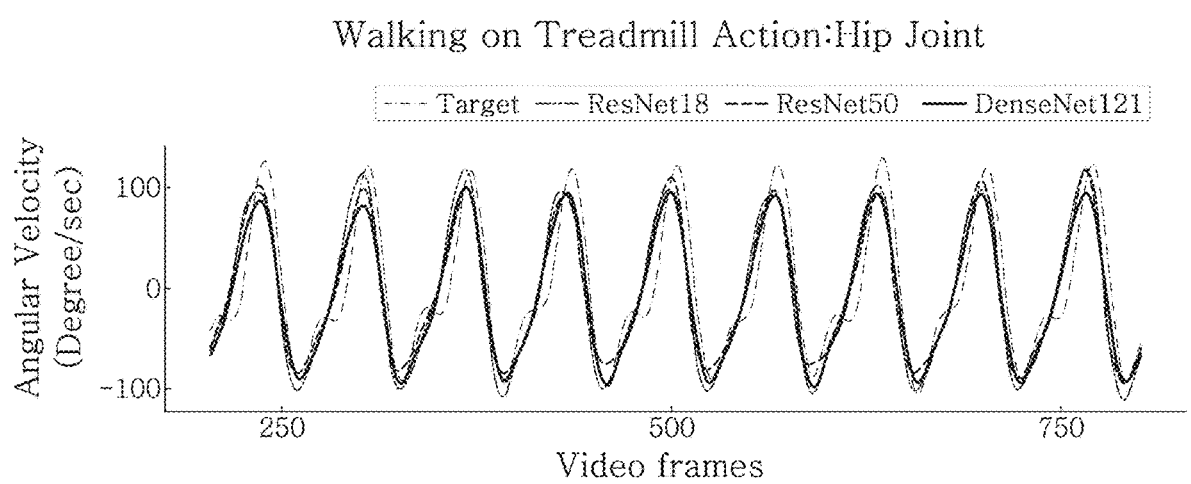
FIGS. 7A to 8C are graphs illustrating the joint angular velocity prediction performance of a predictive model according to an embodiment of the present invention.
Figure 7B:
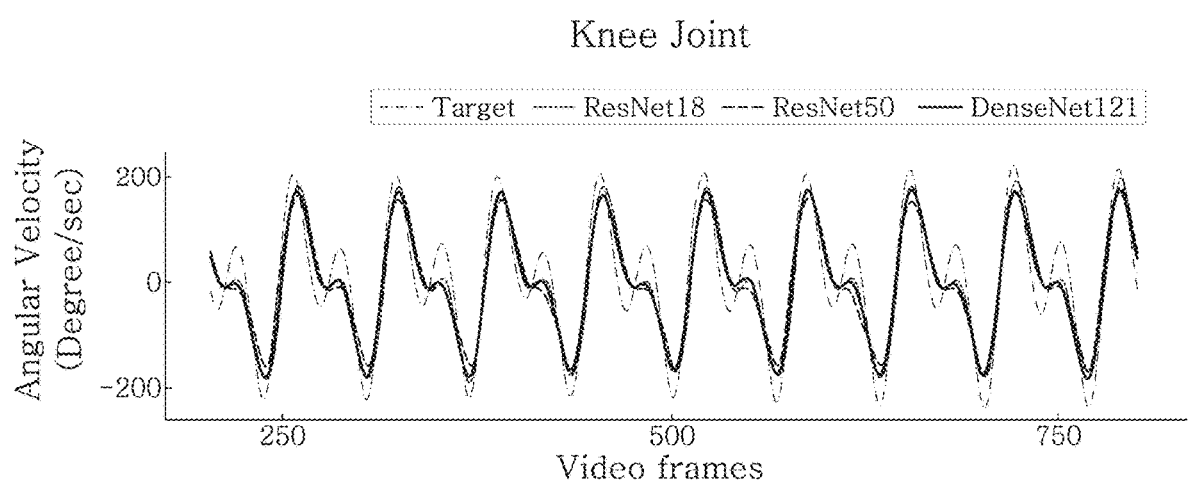
Figure 7C:
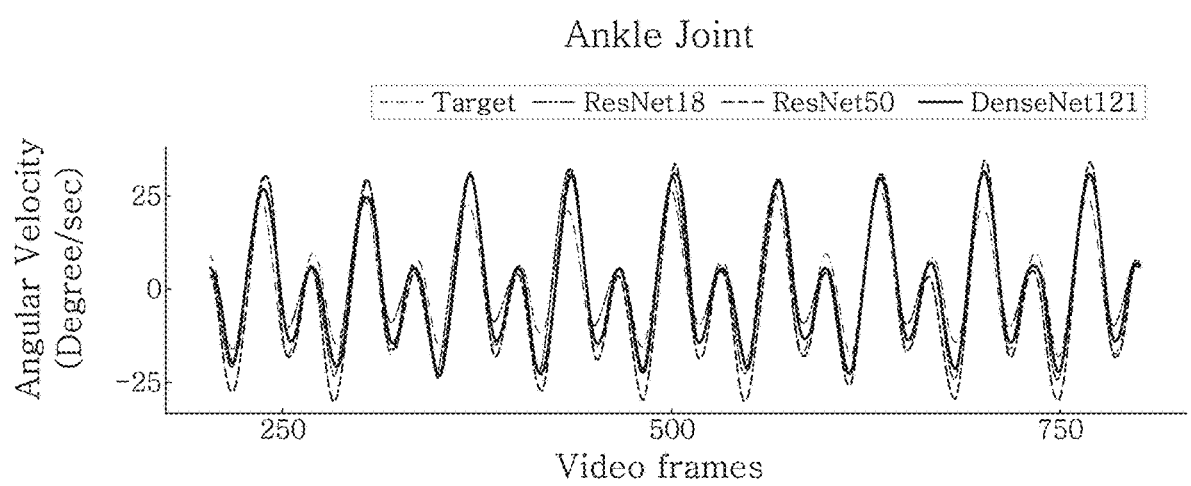

FIGS. 7A to 8C are graphs illustrating the joint angular velocity prediction performance of a predictive model according to an embodiment of the present invention. Specifically, FIGS. 7A to 7C are graphs of analysis results of the predictive models each constructed based on the subject's action according to the treadmill walking, and Table 1 below shows the $Cc_{norm}$ analysis values of each predictive model.

TABLE 1

| Model | Hip Joint | Knee Joint | Ankle Joint |
|---|---|---|---|
| ResNet18 | 0.80 | 0.94 | 0.84 |
| ResNet50 | 0.85 | 0.94 | 0.84 |
| DenseNet121 | 0.87 | 0.95 | 0.86 |

Figure 8A:
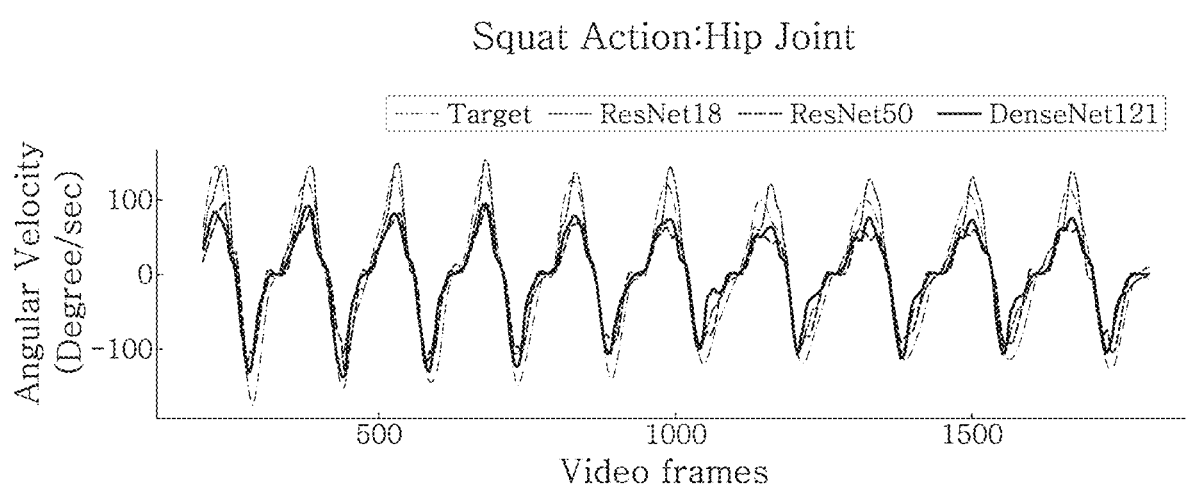
Figure 8B:
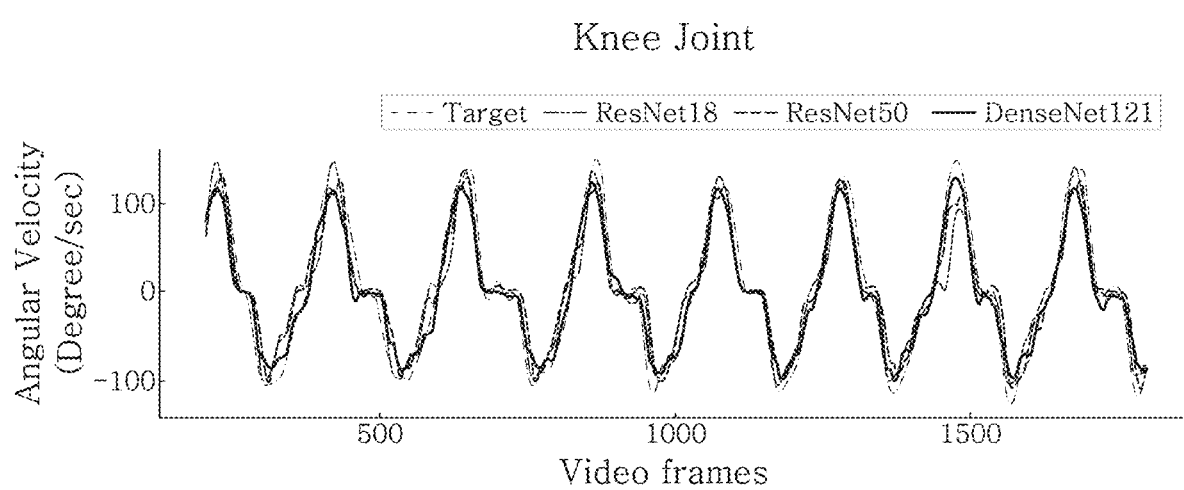
Figure 8C:
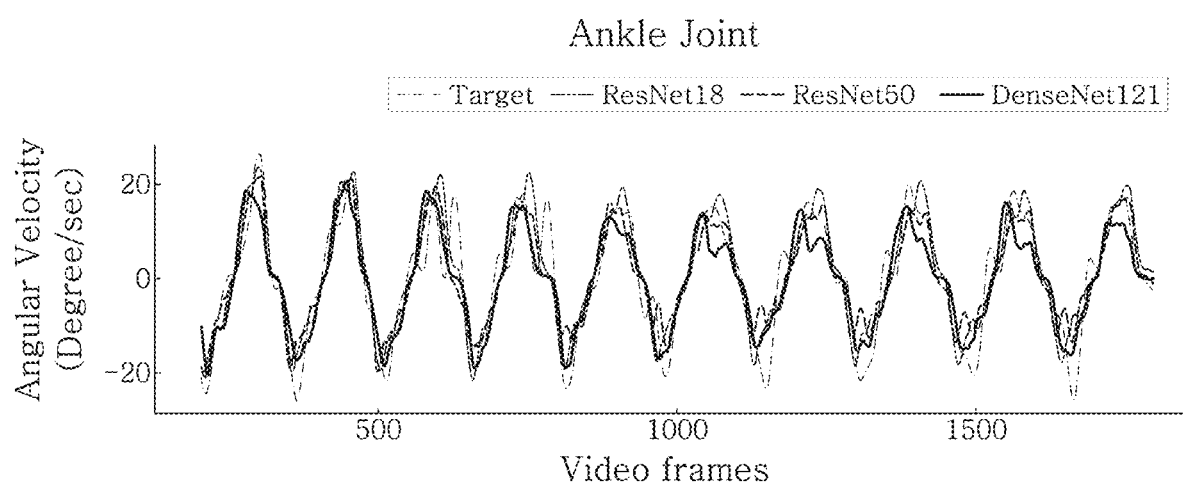

FIGS. 8A to 8C are graphs of performance analysis results of the predictive models, which were constructed based on the action of the subject performing a squat, and Table 2 below shows the $Cc_{norm}$ analysis values of each predictive model.

TABLE 2

| Model | Hip Joint | Knee Joint | Ankle Joint |
|---|---|---|---|
| ResNet18 | 0.87 | 0.94 | 0.90 |
| ResNet50 | 0.86 | 0.92 | 0.91 |
| Dense-Net121 | 0.87 | 0.93 | 0.91 |

As shown in FIGS. 7A to 8C, and Tables 1 and 2, it can be seen that all of the constructed predictive models exhibit high accuracy, and in particular, it can be seen that DenseNet121 exhibits more accurate prediction results compared to other architectures.

Experimental Example 3

In addition, the performance evaluation ($Cc_{norm}$ analysis) was performed on the predictive model trained through the motion images (side view, front view) photographed from different angles, and the results are shown in Table 3 below.

TABLE 3

| Subject | Side view | Front view |
|---------|-----------|------------|
| S18 | 0.89 | 0.90 |
| S30 | 0.91 | 0.82 |
| S31 | 0.90 | 0.91 |
| Average | 0.90 | 0.87 |

As shown in Table 3, the average values of the predictive models trained through the photographed motion images (Side view, Front view) are 0.90 for the side and 0.87 for the front, indicating high prediction ability.

Hereinafter, a method for predicting a three-dimensional human body joint angle using a two-dimensional image according to an embodiment of the present invention will be described.

Figure 9:
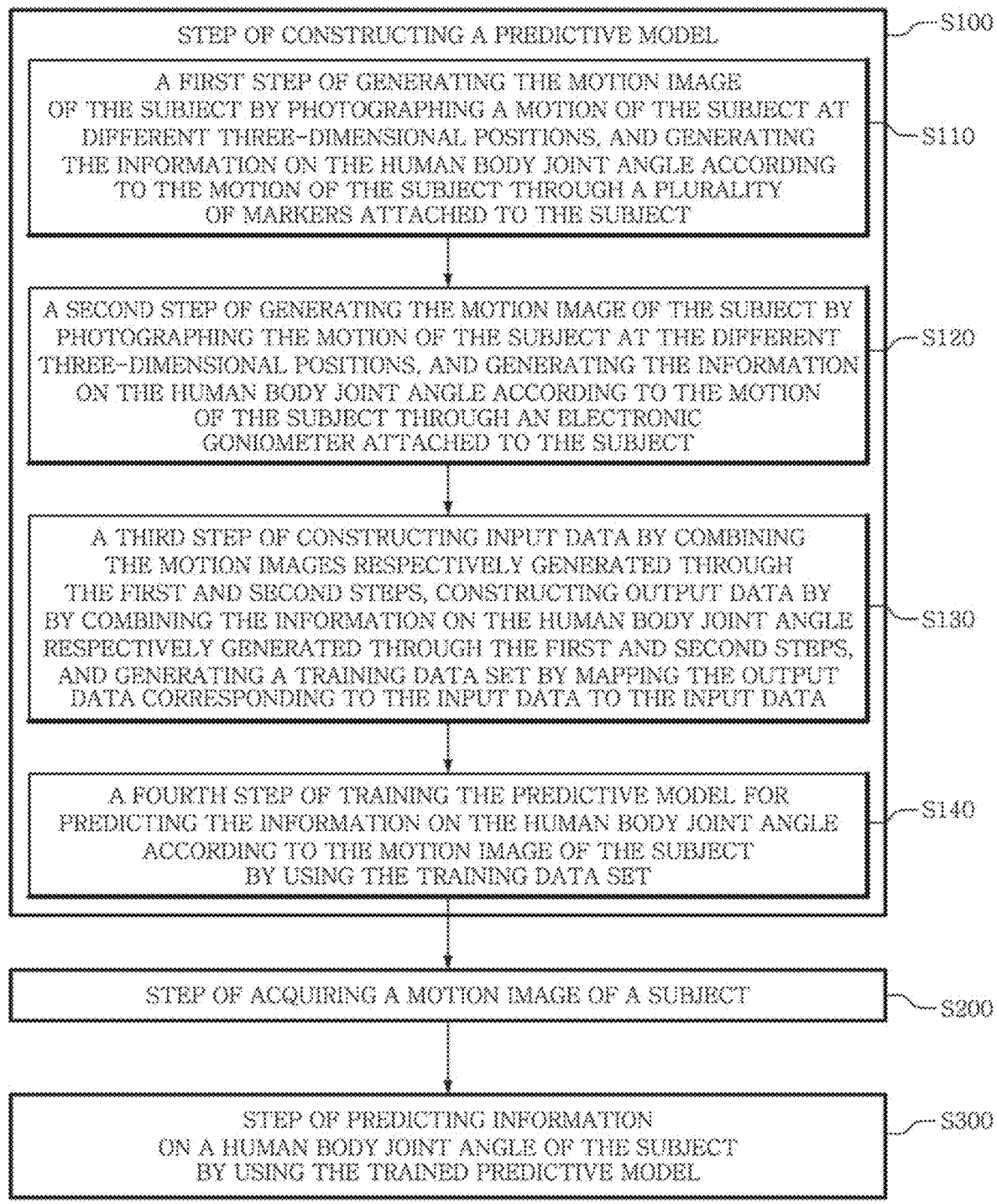
FIG. 9 is a flowchart of a method for predicting a three-dimensional human body joint angle using a two-dimensional image according to an embodiment of the present invention.

FIG. 9 is a flowchart of a method for predicting a three-dimensional human body joint angle using a two-dimensional image according to an embodiment of the present invention. The method may be performed in the system described above, and FIGS. 1 to 5 may be referred to for explanation in the present embodiment.

Referring to FIG. 9, the method for predicting a three-dimensional human body joint angle using a two-dimensional image according to an embodiment of the present invention includes the steps of constructing a predictive model (S100), acquiring a motion image of a subject (S200), and predicting information on a human body joint angle of the subject by using the trained predictive model (S300). In addition, the step (S100) of constructing a predictive model includes a first step of generating a motion image of the subject by photographing the subject's motion at different three-dimensional positions, and generating the information on the human body joint angle according to the subject's motion through a plurality of markers attached to the subject (S110); a second step of generating the motion image of the subject by photographing the subject's motion at the different three-dimensional positions, and generating the information on the human body joint angle according to the subject's motion through an electronic goniometer attached to the subject (S120); a third step of constructing input data by combining the motion images respectively generated through the first and second steps, constructing output data by combining the information on the human body joint angle respectively generated through the first and second steps, and generating a training data set by mapping the output data corresponding to the input data to the input data (S130); and a fourth step of training the predictive model for predicting the information on the human body joint angle according to the motion image of the subject by using the training data set (S140).

In an embodiment, the information on the human body joint angle includes the three-dimensional angle of at least one of the subject's ankle, knee, hip joint, elbow, and torso and the three-dimensional angular velocity of at least one of the subject's ankle, knee, hip joint, elbow and torso. The predictive model predicts the three-dimensional joint angle of at least one of the subject's ankle, knee, hip joint, elbow and torso according to the subject's motion image, and may be constructed to predict the three-dimensional joint angle of at least one of the subject's ankle, knee, hip joint, elbow and torso according to the motion image of the subject.

In an embodiment, the motion image of the subject may include at least one of a gait image of the subject walking on a general flat ground; a treadmill gait image of the subject walking on a treadmill; an exercise motion image of the subject performing an exercise motion; and a daily life motion image of the subject performing a motion occurring in daily life.

In an embodiment, the third step may include performing the preprocessing of applying the YOLO algorithm and tracking the subject in a motion image to generate a bounding box, extracting the subject from the image based on the generated bounding box, and then adjusting the size of the motion image to a predetermined size.

In an embodiment, the predictive model may be constructed through a deep learning.

In an embodiment, the electronic goniometer may not be exposed to the outside by being covered by the clothes the subject is wearing.

The operations by the method for predicting a three-dimensional human joint angle using a two-dimensional image according to the above-described embodiments may be at least partially implemented as a computer program and may be recorded in a computer readable medium. The computer readable medium in which the program for implementing the operations by a method for predicting a three-dimensional human body joint angle using a two-dimensional image according to embodiments is recorded includes any kind of recording device storing the data that can be read by a computer. Examples of the computer-readable recording medium include ROM, RAM, CD-ROM, a magnetic tape, a floppy disk, an optical data storage device, and the like. In addition, the computer-readable recording medium may be distributed in a network-connected computer system, and may store and execute the computer-readable code in a distributed manner. In addition, the functional programs, codes, and code segments for implementing the present embodiment may be easily understood by those skilled in the art to which the present embodiment belongs.

Although described above with reference to the embodiments, the present invention should not be construed as being limited by these embodiments or drawings, and it will be understood by those skilled in the art that various modifications and changes can be made in the present invention without departing from the spirit and scope of the present invention as set forth in the following claims.

What is claimed is:

1. A system for predicting a three-dimensional human body joint angle using a two-dimensional image, comprising:
    a first training data generator configured to include a plurality of cameras that generates a motion image of a subject by photographing a motion of the subject to which a plurality of markers is attached at different three-dimensional positions, and an optical motion analyzer that is configured to generate information on a human body joint angle according to the motion of the subject through the plurality of markers;
    a second training data generator configured to include the plurality of cameras that generate the motion image of the subject by photographing the motion of the subject to which an electronic goniometer is attached at the different three-dimensional positions, and an electronic angle analyzer that is configured to generate the information on the human body joint angle according to the motion of the subject through the electronic goniometer;
    a training data set constructor configured to construct input data by combining the motion images respectively provided from the first training data generator and the second training data generator, construct output data by combining the information on the human body joint angle respectively provided from the first training data generator and the second training data generator, and generate a training data set by mapping the output data corresponding to the input data to the input data;

a model trainer configured to train a predictive model for predicting the information on the human body joint angle according to the motion image of the subject using the training data set; and a joint angle predictor configured to predict the information on the human body joint angle of the subject based on the motion image of a new subject using the trained predictive model.

2. The system according to claim 1, wherein the information on the human body joint angle includes a three-dimensional angle of at least one of the subject's ankle, knee, hip joint, elbow and torso and a three-dimensional angular velocity of at least one of the subject's ankle, knee, hip joint, elbow and trunk, the predictive model is configured to predict a three-dimensional joint angle of at least one of the subject's ankle, knee, hip joint, elbow and torso according to the subject's motion image, and the three-dimensional joint angle velocity of at least one of the subject's ankle, knee, hip joint, elbow and torso according to the subject's motion image.

3. The system according to claim 2, wherein the motion image of the subject includes at least one of a gait image of the subject walking on a general flat ground, a treadmill gait image of the subject walking on a treadmill, an exercise motion image of the subject performing an exercise motion, and a daily life motion image of the subject performing a motion occurring in daily life.

4. The system according to claim 1, wherein the training data set constructor is further configured to perform preprocessing of applying a YOLO algorithm, tracking the subject in the motion image to generate a bounding box, extracting the subject from the image based on the generated bounding box, and then adjusting a size of the motion image to a predetermined size.

5. The system according to claim 1, wherein the predictive model is constructed through deep learning.

6. The system according to claim 1, wherein the electronic goniometer is not exposed to an outside because it is covered by a clothes the subject is wearing.

7. A method for predicting a three-dimensional human body joint angle using a two-dimensional image which is performed in a system for predicting the three-dimensional human body joint angle using the two-dimensional image, the method comprising the steps of:

constructing a predictive model;

acquiring a motion image of a subject; and predicting information on a human body joint angle of the subject by using the trained predictive model, wherein the step of constructing a predictive model includes:

a first step of generating the motion image of the subject by photographing a motion of the subject at different three-dimensional positions, and generating the information on the human body joint angle according to the motion of the subject through a plurality of markers attached to the subject;

a second step of generating the motion image of the subject by photographing the motion of the subject at the different three-dimensional positions, and generating the information on the human body joint angle according to the motion of the subject through an electronic goniometer attached to the subject;

a third step of constructing input data by combining the motion images respectively generated through the first and second steps, constructing output data by combining the information on the human body joint angle respectively generated through the first and second steps, and generating a training data set by mapping the output data corresponding to the input data to the input data; and a fourth step of training the predictive model for predicting the information on the human body joint angle according to the motion image of the subject by using the training data set.

8. The method according to claim 7, wherein the information on the human body joint angle includes a three-dimensional angle of at least one of the subject's ankle, knee, hip joint, elbow, and torso and a three-dimensional angular velocity of at least one of the subject's ankle, knee, hip joint, elbow and torso, the predictive model is configured to predict a three-dimensional joint angle of at least one of the subject's ankle, knee, hip joint, elbow and torso according to the motion image of the subject, and is configured to predict the three-dimensional joint angle velocity of at least one of the subject's ankle, knee, hip joint, elbow and torso according to the motion image of the subject.

9. The method according to claim 8, wherein the motion image of the subject includes at least one of a gait image of the subject walking on a general flat ground; a treadmill gait image of the subject walking on a treadmill; an exercise motion image of the subject performing an exercise motion; and a daily life motion image of the subject performing a motion occurring in daily life.

10. The method according to claim 7, wherein the third step further include performing preprocessing of applying a YOLO algorithm and tracking the subject in the motion image to generate a bounding box, extracting the subject from the image based on the generated bounding box, and then adjusting a size of the motion image to a predetermined size.

11. The method according to claim 7, wherein the predictive model is constructed through a deep learning.

12. The method according to claim 7, wherein the electronic goniometer is not exposed to an outside by being covered by a clothes the subject is wearing.

13. A non-transitory computer readable medium which is readable by a computing device and stores a program instruction operable by the computing device, wherein when the program instruction is executed by a processor of the computing device, the processor is configured to perform the method for predicting a three-dimensional human body joint angle using a two-dimensional image according to claim 7.

* * * * *